US00PP19517P2

(12) United States Plant Patent
Bunker

(10) Patent No.: US PP19,517 P2
(45) Date of Patent: Dec. 2, 2008

(54) ***BRACTEANTHA* PLANT NAMED 'FLOBRAELE'**

(50) Latin Name: *Bracteantha bracteata*
Varietal Denomination: FLOBRAELE

(75) Inventor: Kerry V. Bunker, Redland Bay (AU)

(73) Assignee: Floreta Intellectual Property Pty. Ltd. (AU)

( * ) Notice: Subject to any disclaimer, the term of this patent is extended or adjusted under 35 U.S.C. 154(b) by 0 days.

(21) Appl. No.: 11/879,597

(22) Filed: Jul. 18, 2007

(51) Int. Cl.
*A01H 5/00* (2006.01)

(52) U.S. Cl. ..... Plt./359

(58) Field of Classification Search ..... Plt./359
See application file for complete search history.

*Primary Examiner*—Kent L. Bell
*Assistant Examiner*—June Hwu

(57) ABSTRACT

A new and distinct cultivar of *Bracteantha* plant named Flobraele, characterized by its compact plant habit, many flowers per plant, early flowering, narrow leaf width, and by its vibrant burnt orange flowers which are held above the foliage.

1 Drawing Sheet

The present invention relates to a new and distinct cultivar of *Bracteantha* plant, botanically known as *Bracteantha bracteata,* and referred to by the variety denomination Flobraele. The genus and species were formerly known as *Helichrysum bracteatum,* and *Bracteantha bracteata* is synonymous with the more recent botanical designation *Xerochrysum bracteatum.* The species is also known by the common names strawflower, paper daisy, and everlasting daisy.

The new cultivar is the product of a planned breeding program carried out by the inventor in Redland Bay, Australia during February 2003. The objective of the breeding program was to create new cultivars having compact bush habit, narrower leaves, and flower heads or inflorescences covering a range of colors and held above the foliage on short peduncles.

The female or seed parent was unpatented Proprietary Selection 01-563. The characteristics of the female parent are flower heads with many magenta bracts, short peduncles, and large broad leaves. The male or pollen parent was unpatented Proprietary Selection 01-566. The characteristics of the male parent are few red bracts, few flowers per bush, flower heads held above the foliage on short peduncles, and medium broad leaves.

The first act of asexual reproduction of the new cultivar was accomplished when vegetative cuttings were made from the selection in October 2003 and grown in a controlled environment in Redland Bay, Australia under the supervision of the inventor. Horticultural examination of controlled flowerings of successive plantings has shown that the unique combination of characteristics of the new cultivar are firmly fixed and are retained through successive generations of asexual reproduction.

The new cultivar has not been observed under all possible environmental conditions. The phenotype may vary significantly with variations in environment such as temperature, light intensity, fertilization levels, and day length without, however, any variance in genotype. The following observations, measurements and comparisons describe plants grown in Redland Bay, Queensland, Australia under normal commercial growing conditions. The age of the plant described is 16 weeks.

SUMMARY OF THE INVENTION

The following traits have been repeatedly observed and have been determined to be basic characteristics of the new cultivar, which in combination distinguish the new cultivar as being new and distinct:

1. Vibrant burnt orange flowers
2. Compact plant habit
3. Many flowers per bush
4. Early flowering
5. Narrow leaf width
6. Flowers held above the foliage on short peduncles The new cultivar differs from its male parent by its flower color, narrower leaf width, and more flowers per bush. Compared to its female parent, the new cultivar differs therefrom by flower color, narrower leaf width, and more flowers per bush.

Of the many commercial cultivars known to the present inventor, the most similar in comparison to the new cultivar is the cultivar Flobrafla, disclosed in U.S. Plant Pat. No. 16,950. In comparative testing conducted in Redland Bay, Queensland, Australia, plants of the new cultivar differ from plants of the comparison cultivar in the characteristics described in Table 1:

TABLE 1

| Trait | 'FLOBRAELE' | 'FLOBRAFLA' |
|---|---|---|
| Flower color | burnt orange | yellow and red |
| Leaf width | narrow | medium |

BRIEF DESCRIPTION OF THE PHOTOGRAPHS

The top photograph shows an overall view of a typical flowering plant of the new cultivar, grown in a 14 cm container for about 10 weeks.

The bottom photograph shows a close up of a typical inflorescence.

The photographs show the colors as true as is reasonably possible with colored reproductions of this type. If any differences exist between the photographic color and the color values described below, the values in the detailed description are accurate.

DETAILED BOTANICAL DESCRIPTION

In the following description color references are made to The Royal Horticultural Society Colour Chart. The values are based on plant material 16 weeks old grown in Redland Bay, Queensland, Australia, and the values were taken on approximately Jun. 25, 2007.

Botanical classification: *Bracteantha bracteata* 'Flobraele'.

*Seed parent.*—Proprietary Selection 01-563.

*Pollen parent.*—Proprietary Selection 01-566.

Propagation:

*Type.*—Shoot tip cutting.

*Time and temperature to initiate roots.*—Summer, about 21 to 28 days at 20 to 25 deg. C. in the greenhouse; Winter, about 28 to 35 days at 15 to 20 deg. C. in the greenhouse.

*Rooting description.*—Freely branching, fibrous, root density moderate, color pale brown.

Plant description:

*General appearance and form.*—Compact and bushy growth habit; upright, outwardly spreading and rounded plant form with dense foliage and inflorescences held above the foliage on short peduncles. Plant diameter approximately 35 cm and plant height approximately 15 cm.

*Growth and branching habit.*—Freely branching with lateral branches forming at every node to produce a dense and bushy plant.

*Plant habit.*—Rounded, compact, highly branched, and vigorous.

*Plant height (from soil level to the top of a mature plant grown in a 14 cm container).*—15 cm.

*Plant diameter.*—30 cm.

*Time to produce mature plant.*—After rooting, about 10 weeks are required to produce finished flowering plants in 14 cm. pots.

Branches:

*Number of branches per plant.*—85.

*Length.*—8.5 cm.

*Width.*—3.5 mm.

*Internode length.*—About 1.5 cm.

*Orientation.*—Upright, mounding.

*Texture.*—Slightly pubescent.

*Color.*—195D.

Foliage description:

*Leaf shape.*—Linear elliptic.

*Arrangement.*—Alternate, single, sessile.

*Length.*—About 8.0 cm.

*Width.*—About 9.5 mm for leaves in the upper and middle regions of the plant. There are typically 8–10 persistent juvenile leaves near the bottom which are 15–20 mm in width.

*Shape at apex.*—Acute.

*Shape at base.*—Sessile.

*Margin.*—Entire.

*Color of young foliage.*—Upper surface: 146 B. Lower surface: 146 B.

*Color of mature foliage.*—Upper surface: 137 C. Lower surface: 137 D.

*Venation pattern.*—Pinnate.

*Leaf texture.*—Upper and lower surfaces are very weakly pubescent.

*Venation color.*—Upper surface 137 C, lower surface 137 D.

Inflorescence description:

*Flower type.*—Single daisy-type composite inflorescent form; involucral bracts and disc florets arranged acropetally on capitulum.

*Natural flowering season.*—Natural flowering season is year-round in Redland Bay, Queensland, Australia.

*Quantity of inflorescences.*—At one time, more than 81 open flowers and buds per plant.

*Bud.*—Rate of opening (from showing color to fully open flower): 14 to 21 days. Length: About 20 mm. Diameter: About 8.5 mm. Shape: Broadly ovoid with acute apex. Color: Yellow orange 22A with greyed orange 176 A streaks toward the apex; greyed red 180 A tips at the top of the bud.

*Inflorescence.*—Inflorescence depth: About 1.5 cm. Inflorescence diameter: About 4.0 cm.

*Fragrance.*—Sweet vanilla fragrance of medium intensity.

*Involucral bracts.*—Quantity per inflorescence: About 63 in multiple whorls. Length: 14 mm. Width: 4.0 mm. Shape: Ligulate, concave. Apex: Acute. Base: Truncate. Margin: Entire. Texture: Both surfaces, smooth, glabrous, papery, satiny. Color, Upper surface when opening: greyed orange 171A blending to yellow orange 21 A at the base; lower surface when opening: greyed orange 171A blending to yellow orange 21A at the base. Upper surface, fully opened flower: outer involucral bracts are orange 26A blending to yellow orange 21A toward the base. Inner involucral bracts are entirely yellow orange 21A. lower surface, opened flower: greyed orange 171A streaks overlaying a base color of yellow orange 21A.

*Disc florets.*—Three forms of female filiform florets surround the perimeter of the disc, with androecium not being present in these florets; the remainder of the disc is covered with bisexual disc florets containing both androecium and gynoecium reproductive organs.

*Bisexual disc florets.*—Shape: Tubular with five lobes. Length of individual floret: 7.0 mm. Width of individual floret: 1.0 mm. Quantity: 328. Diameter of mature disc: 11.5 mm. Color, immature discs: 23 B. Color, Mature discs: 23 A.

*Peduncle.*—Strength: Strong. Angle: Upright, erect. Length: 2.0 cm. Color: 195 D.

*Surface texture.*—Medium woolly pubescence.

Reproductive organs:

*Androecium.*—Anther color: 23 B. Anther shape: Fused anther tube with five long thin linear anthers surrounding the style. Anther length: Minute. Pollen color: Yellow.

*Gynoecium.*—Pistil length: About 8.5 mm. Stigma shape: Bi-parted. Stigma color: 23 B. Style length: About 7.0 mm. Style color: 23 B. Ovary color: No color to describe it because of its minute size.

Seed: No seed was noted on the specimen plants observed.

Disease/pest susceptibility: Plants of the new *Bracteantha* have not been observed to be abnormally resistant to pathogens or pests common to *Bracteantha*.

Temperature tolerance: Plants have not been observed to cease flowering at the temperatures observed at Redland Bay, Queensland, Australia.

Growth retardants: No growth retardants are required for commercial production of this cultivar, and none were used on the plants observed in this description.

I claim:

1. A new and distinct cultivar of *Bracteantha* plant named Flobraele, as illustrated and described.

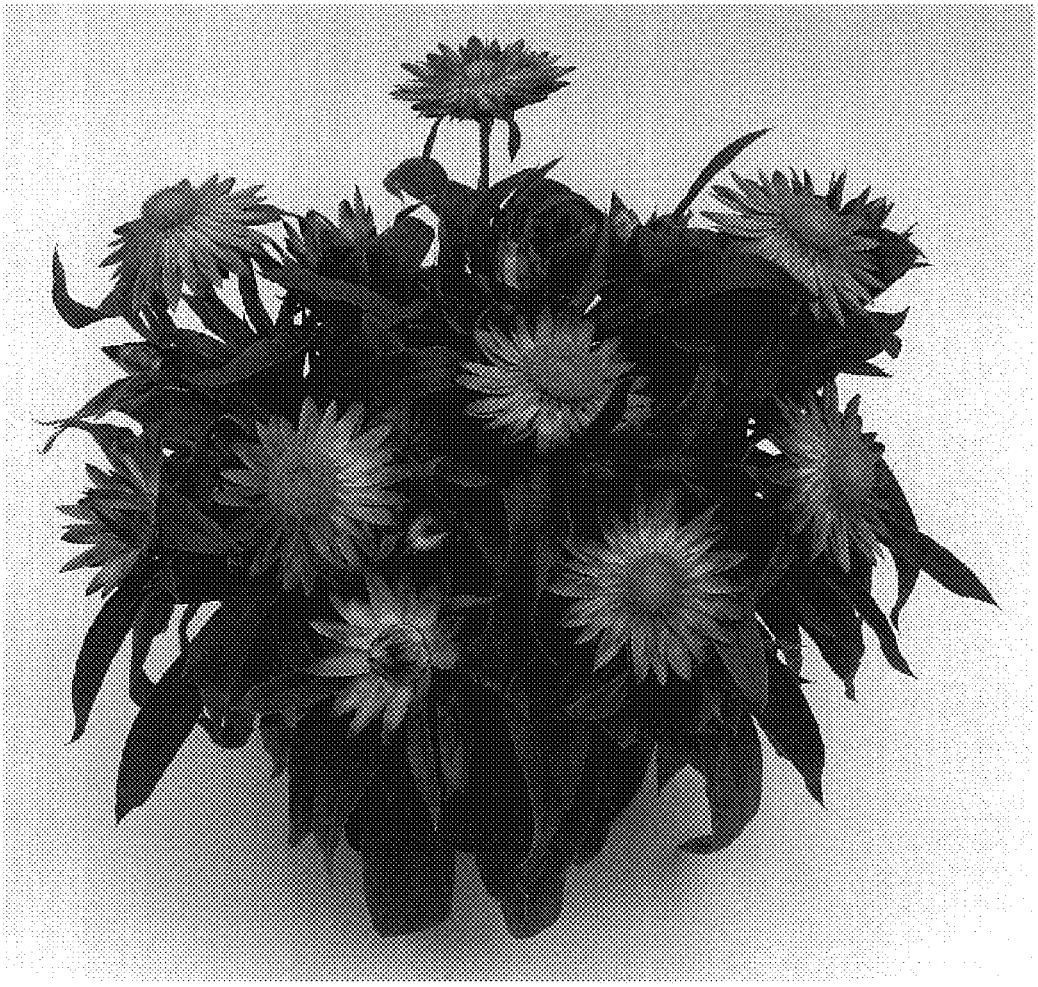
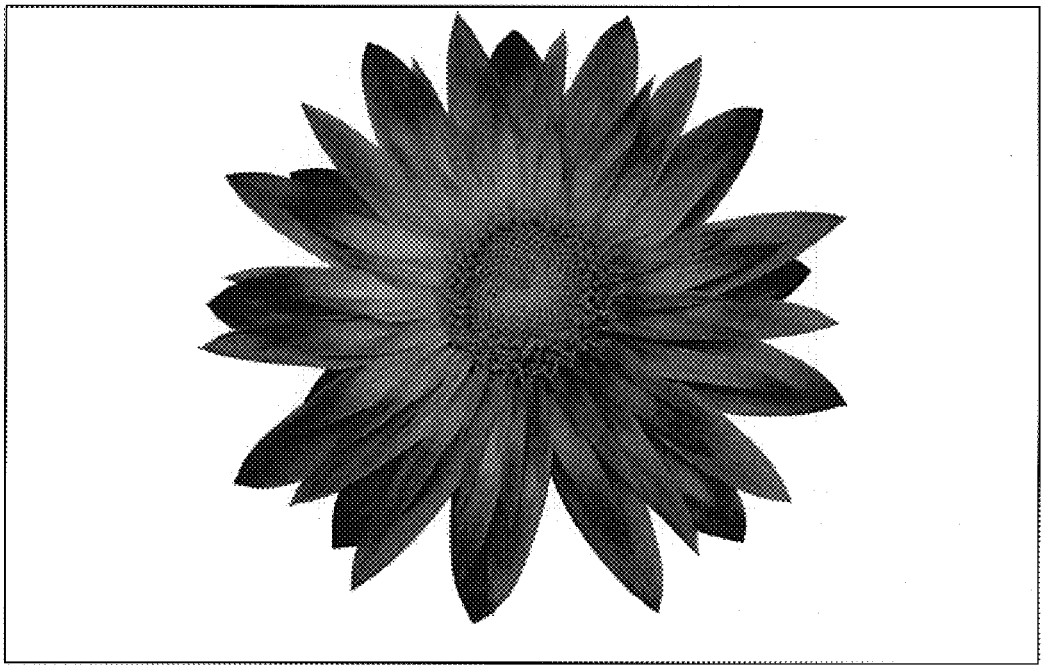

* * * * *